United States Patent [19]

DeVoid et al.

[11] 4,211,018

[45] Jul. 8, 1980

[54] APPARATUS AND PROCEDURE FOR TESTING PREREQUISITE SKILLS FOR READING BY USE OF A DYNAMIC LINE PATTERN

[76] Inventors: Robert R. DeVoid, Box 593 Tower Hill Farm, Hinsdale, N.H. 03451; William A. Hodson, Box 413 Putney, Putney, Vt. 05346

[21] Appl. No.: 827,876

[22] Filed: Aug. 26, 1977

[51] Int. Cl.$^2$ ............................................. G09B 17/00
[52] U.S. Cl. ............................................................. 35/35 R
[58] Field of Search ................ 35/35 R, 35 H, 36, 37, 35/8 R, 9 R, 22 R; 40/442

[56] References Cited

U.S. PATENT DOCUMENTS

| | | | |
|---|---|---|---|
| 177,120 | 5/1876 | Harvey | 35/36 |
| 3,452,456 | 7/1969 | Tinman | 35/34 |
| 3,469,325 | 9/1969 | Greenberg | 35/9 R |
| 3,672,074 | 6/1972 | Huffstetter | 35/35 H |
| 3,715,822 | 2/1973 | Hansen, Jr. et al. | 40/442 |
| 3,774,318 | 11/1973 | Sterriti | 35/35 R |
| 3,800,443 | 4/1974 | O'Connell et al. | 35/35 H |
| 4,112,597 | 9/1978 | Seaver | 35/36 |

*Primary Examiner*—William H. Grieb
*Attorney, Agent, or Firm*—Wolf, Greenfield & Sacks

[57] ABSTRACT

Visual perception and related skills are tested to assess the level of a person's prerequisite skills for reading. An apparatus is operated by a qualified examiner to generate visual line patterns that the child must recall and reproduce. The testing apparatus comprises a control box and a display panel interconnected by a multi-wire cable. Two of eight control buttons (switches) spatially arranged in an eight-pointed star, are selectable by the examiner to generate a moving line pattern on the display which may be any one of a number of patterns moving between predetermined points on the display corresponding to the points of the star. The line patterns on the display each progress from a point of the star, to the center of the star and out to a second preselected point to thereby generate 45°, 90°, 135° or 180° patterns. A control is provided so that the patterns can be generated at different rates of say 0.25, 0.50, or 1.0 second per pattern. The testing procedure takes place in stages with the child being required to reproduce a single line pattern, one of a number of different patterns, and more than one pattern. Preferably a total of 26 different test categories are to be recorded, and the examiner evaluates the test results with the aid of scoring templates to determine scores for basic pattern reproduction, spatial orientation, line quality, directionality, mental processing time, visual short term memory, and visual sequencing memory.

24 Claims, 6 Drawing Figures

APPARATUS AND PROCEDURE FOR TESTING PREREQUISITE SKILLS FOR READING BY USE OF A DYNAMIC LINE PATTERN

BACKGROUND OF THE INVENTION

The present invention relates to an apparatus and the associated testing procedure for determining the visual perception and related skills of a person. The apparatus and procedure of the present invention is usually used for the testing or pre-school or elementary school children or others to determine the possible causes of any reading deficiency that they may have.

An objective of the present invention is to develop an apparatus and associated test which could be used to predict the incidence of reading deficiency in children and which could also be used to diagnose specific aspects of the deficiency early enough to provide effective remediation. Reading deficiency may result from a variety of problems including visual or auditory dyslexia, environmental deprivation, emotional disturbances, aphasia, or autism. There presently exist reading and visual perception tests that are used for children such as the Gates-MacGinitie Reading Test or the Developmental Test of Visual Perception. However, these tests are generally static tests that evaluate the reading of text or letters.

The existing tests do not provide sufficient criteria for the assessment of the visual perception capabilities of a subject. Visual perception has been found to be a crucial factor especially in the early development of reading skills. Accordingly, one object of the present invention is to provide a test designed to measure a number of those aspects of the subject's visual perception and related capabilities which have been linked to such reading deficiency as, for example, dyslexia.

Another object of the present invention is to provide an operational method for the early diagnosis of reading deficiencies so as to provide a basis for effective remediation.

In accordance with this invention a dynamic-type of test is used involving the generation of moving line patterns. The measurable characteristics fall into seven categories including basic pattern reproduction, spatial orientation, line quality, directionality, mental processing time, short-term visual memory, and visual sequencing memory.

SUMMARY OF THE INVENTION

To accomplish the foregoing and other objects of this invention, there is provided an apparatus in the form of a sequencer for establishing a plurality of different line patterns which are to be visually perceived and reproduced by the person being tested. The sequencer comprises generally a display and control means for selectively generating a plurality of different line patterns each comprising at least one line segment with the majority of the patterns comprising two line segments extending in different directions. The patterns that are generated include 45°, 90°, 135° and 180° patterns. In accordance with the test procedure the line patterns are to be copied by the person being tested, and are scored to determine the basic or inherent reading capabilities of the person. In the sequence of testing, the subject is required to reproduce single patterns, one of a number of different patterns shown the subject, and also is required to reproduce in sequence a series of patterns previously shown. Scoring is made in the following categories; basic pattern reproduction, spatial orientation, line quality, directionality, mental processing time, short term visual memory, and visual sequencing memory.

In one embodiment the line sequencer apparatus comprises a control box and a display panel which are interconnected by a multiwire cable. The controls on the control box include an on-off switch, a reset button, a variable speed knob, and eight buttons or switches arranged at the points about an 8-pointed star. The display panel preferbly comprises a translucent screen and a plurality of light emitting means such as light emitting diodes similarly arranged in an 8-pointed star with preferably seven diodes arranged in each of the eight legs of the star and one center diode. The eight control buttons correspond to the eight points of the star on the display.

The control electronics comprises a pair of counters and a memory. A pattern is produced on the display panel by pushing a first button representative of the place where the pattern is to start on the star and then pushing a second button corresponding to the place where the pattern is to end. The memory stores both of these button addresses and also the sequence of selection of these button addresses. Upon activation of the second button the operations counter enables the display and the diodes are illuminated in sequence under control of the clock counter from the outer diode to the center diode along the leg of the star corresponding to the first button depressed. The clock counter is then conditioned to count in the opposite direction along the second selected leg terminating the line at the point on the star on the display corresponding to the second selected button. At the termination of the generation of a line pattern, the operations counter reverts to its reset count thereby automatically resetting the circuitry and preparing it for a further line pattern generation.

In accordance with the testing procedure of this invention as each line pattern is generated by the examiner a person being tested is required to reproduce the line pattern. The examiner can note the accuracy of the reproduction, and scoring of perception is possible with the further use of overlay templates used by the examiner in assessing the accuracy of the reproduced line pattern according to certain criteria. Thus, templates are preferably used in grading in this manner. The test also preferably includes generation of a number of different patterns in sequence with the person being tested required to select one of the patterns previously shown so as to test short term visual memory of the person being tested. Further, the person is required to reproduce a plurality of previously shown patterns in sequence so as to test his visual sequencing memory capabilities. The examiner makes a scoring determination based upon observing the basic correctness of the reproduced line patterns, their directionality accuracy, and the mental processing time of the subject in reacting to the patterns. The examiner also uses overlay templates so as to score for basic pattern reproduction, spatial orientation and line quality.

In the preferred embodiment the line patterns are all displayed with essentially two line segments, both of which form the legs of an 8-pointed star. However, in an alternate embodiment the line patterns may be displayed in a different manner. Also, the line patterns are preferably depicted by a rapidly moving line, but also could be depicted by a display of the entire pattern that is subsequently blanked from one end to the other. This is simply another form of a dynamic line pattern. In an alternate embodiment the line segments may be arranged in the form of a square rather than a star with the diagonals of the square being used for generating line patterns.

DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figure 1:
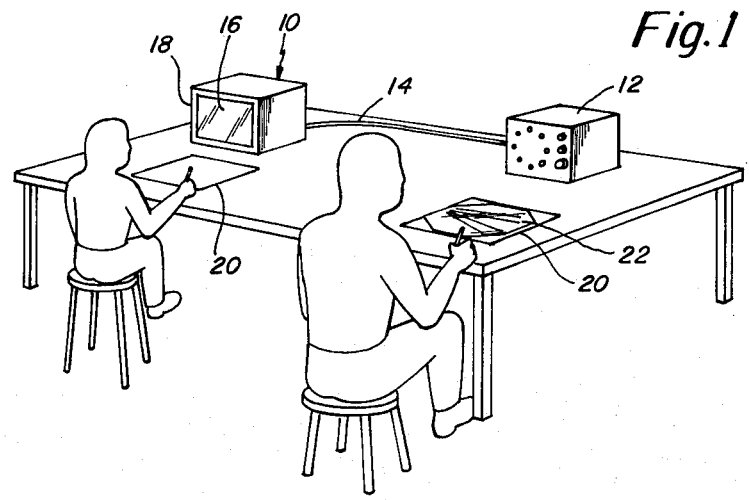
FIG. 1 is a perspective view showing the apparatus of the present invention controlled by an examiner for testing the pre-requisite reading capabilities of a person.
Figure 3:
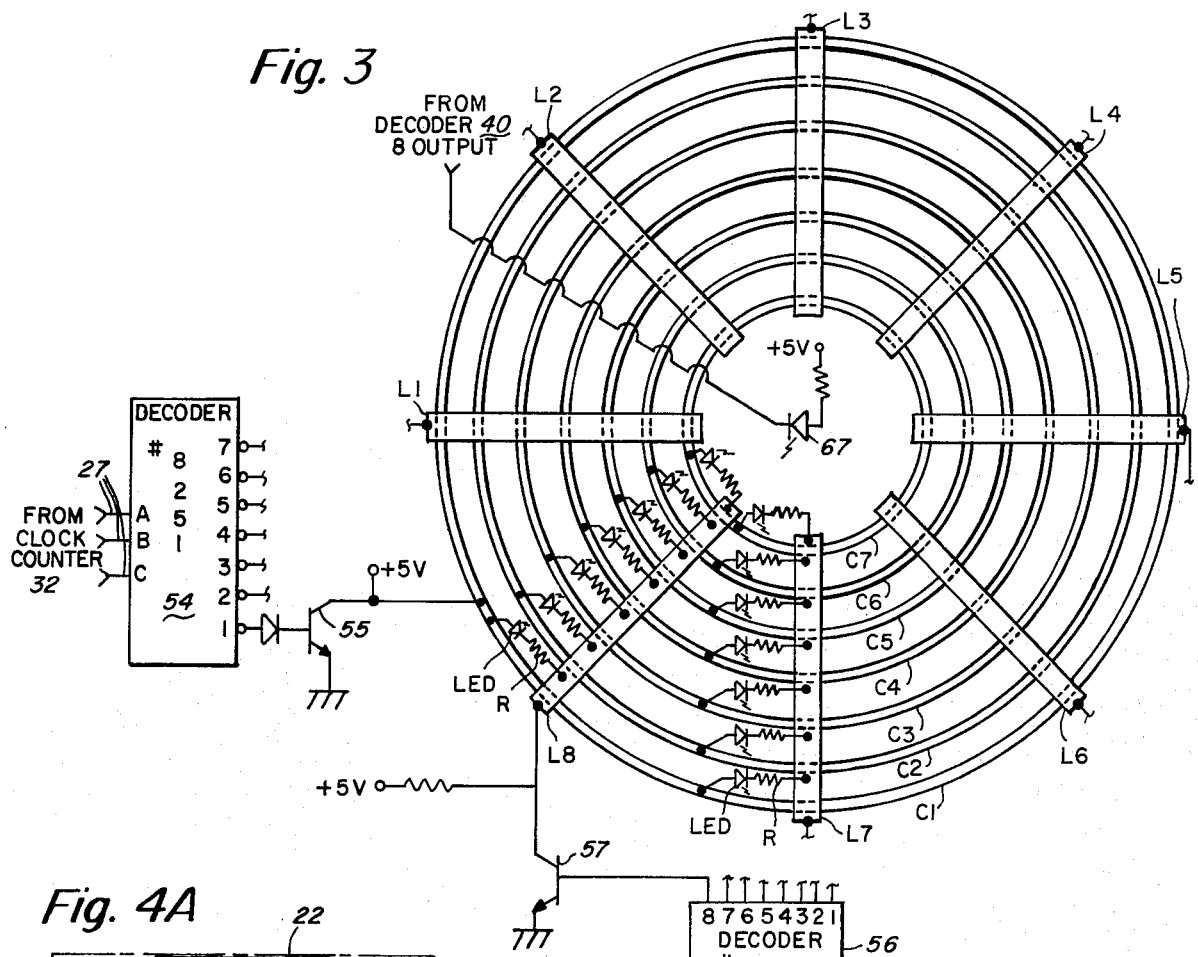
FIG. 3 is a circuit block diagram of the display panel shown in FIGS. 1 and 2.

FIG. 1 shows in a perspective view the apparatus of the present invention disposed on a table or other support structure and including a display 10 and a control box 12 interconnected by a multi-wire cable 14. The display 10 has a square white fiberglass screen 16 which may be 13" square and about the periphery of the screen there is a 1" black border 18. Behind the translucent screen 16, there are light emitting diodes which are arranged in an 8-point star. FIG. 3 shows the display in more detail as will be discussed hereinafter.

FIG. 1 shows a child seated facing the display 10 with a work paper 20 disposed in front of the child. An examiner is seated next to the child at the control box 12 where the examiner has control of all line patterns generated on the translucent screen 16. FIG. 1 also shows a work paper of the child being scored by the examiner and the use of an overlay template 22 used by the examiner as an aid in scoring the line pattern reproduction. In reality the scoring is done after the test.

The control box 12 has eight control buttons in the preferred embodiment also arranged in an 8-pointed star. A pattern is produced on the display panel by first pushing a button where the pattern is to start on the star, and then pushing a second button where the pattern is to end. The control electronics operates so that after both buttons have been depressed, the light emitting diodes illuminate in sequence inwardly along one leg of the star and outwardly along the other selected leg of the star to create line patterns on the display of 45°, 90°, 180° or 135°. In the simplest test sequence a child is requested to reproduce each line pattern generated by the examiner on the work paper 20. A separate work paper is preferably used on each line pattern that is to be reproduced. The examiner also has available at the control box 12 an on-off switch, a speed control for controlling the rate of the generated line patterns, and a reset button.

Figure 2:
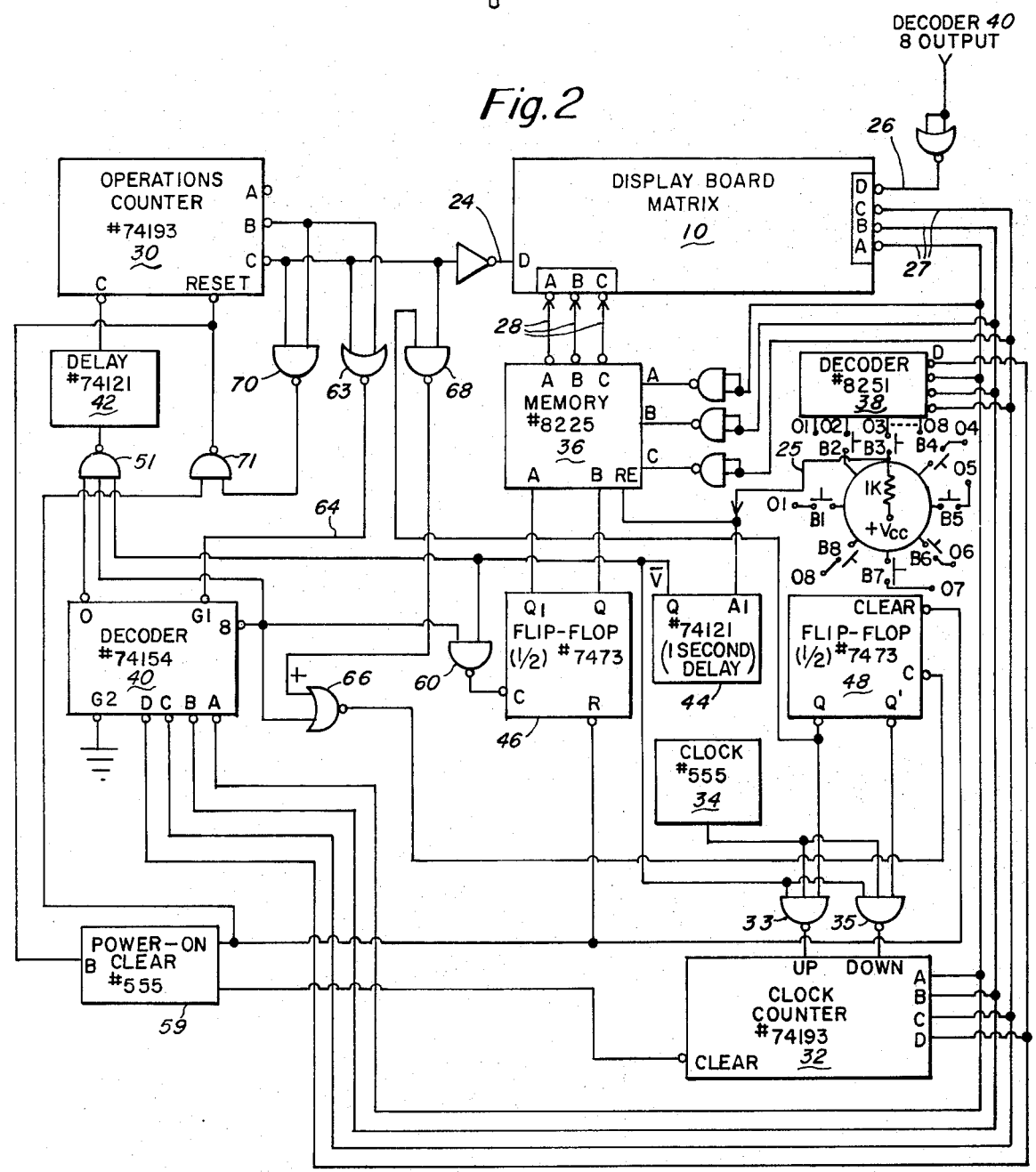
FIG. 2 is a logic block diagram of a preferred construction for the control box shown in FIG. 1.

FIG. 2 is a logic diagram showing the electronics within the control box 12 and also the display 10 which is shown in more detail in FIG. 3. Line 24 to the display is an enable line, line 26 to the display illuminates the center light emitting diode, and lines 27 and 28 represent two different addresses; one address is for identifying the selected legs of the line pattern while the other address controls the movement along each of the selected legs commencing from the outer end of one leg to the center and from there outwardly to the outer end of the other selected leg.

The control logic of FIG. 2 includes an operations counter 30, a clock counter 32, a main clock 34, memory 36 and decoders 38 and 40. In addition, there are a number of control logic gates, delay networks 42 and 44, and flip-flops 46 and 48. FIG. 2 does not show the circuitry for powering the different integrated circuits shown in FIG. 2 as this is well-known power supply circuitry including, for example, a transformer for receiving 110 volt AC, a rectifier and a regulator for converting the voltage to a low DC voltage, such as 5 volt DC.

The basic timing is accomplished by the clock 34 which is a variable speed clock of the type 555. The speed control knob on the control box may control a potentiometer in the clock to vary the clock pulse frequency from the clock. The basic programming of the electronics is accomplished by the operations counter 30 which has outputs A, B and C, a reset input and a clock input coupled by way of delay 42 and controlled by the NAND gate 51.

The clock counter 32 is connected as an up/down counter having its outputs A, B, C and D coupled to the display 10 and also to the decoders 38 and 40. The clock counter 32 controls the sequencing along a line (leg) as previously indicated. The actuation of two control buttons defines the line pattern and the addresses of these control buttons are stored in the memory 36. Detection of the actuated button occurs by way of the decoder 38.

The flip-flop 46 is operated to control the memory 36 as to which address is to be read out of memory. The flip-flop 48 controls the clock counter for counting either up or down.

FIG. 3 shows the display matrix which is located behind the translucent screen 16. This matrix will be discussed in more detail hereinafter. However, in regard to the operation of FIG. 2, the clock counter signals coupled by way of decoder 54 control the conductive circles C1–C7 while the memory signals on lines 28 coupled by way of decoder 56 control the conductive legs L1–L8. Thus, for example, if legs L1 and L5 have been selected and their addresses are stored in memory 36 this circuitry operates so as to illuminate the light emitting diodes connected to conductive leg L1 from the outer circle C1 to the inner circle C7 and thereafter illuminate the diodes associated with leg L5 from the inner circle to the outer circle thereby generating a horizontal straight line pattern moving from left to right as viewed in FIG. 3.

At power up, the device 59 which may be a type 555 generates a reset signal. The reset signal from the device 59 clears the counters 30 and 32 and resets the flip-flops 46 and 48. At this time it is initially assumed that none of the buttons B1–B8 have been actuated.

Under this initial condition with the operations counter reset to its zero count the operations counter 30 stays in that count until one of the buttons B1–B8 is actuated. The clock counter, however, continuously cycles interrogating each of the buttons B1–B8 by way of the decoder 38 which may be the well known decoder type 8251. Each binary coded decimal signal at the input to the decoder 38 causes in sequence an interrogation of each of the buttons B1–B8.

The following is a truth table for the operations counter showing the sequential decimal counts and the corresponding outputs.

| OPERATIONS COUNTER COUNT | OPERATIONS COUNTER OUTPUT | | |
|---|---|---|---|
| | C | B | A |
| 0 | 0 | 0 | 0 |
| 1 | 0 | 0 | 1 |
| 2 | 0 | 1 | 0 |
| 3 | 0 | 1 | 1 |
| 4 | 1 | 0 | 0 |
| 5 | 1 | 0 | 1 |
| 6 (Reset) | 1 | 1 | 0 |

In the zero position of the operations counter, the display panel is inhibited as the line 24 is at its "high" level. The clock counter 32 is counting up because the up gate 33 is enabled whereas the down gate 35 is inhibited. The flip-flop 48, being reset, has its output Q at its enabling level. Also, the output Q from the delay 44 is at its "high" level and thus upon the occurrence of each clock pulse from clock 34 the counter 32 is counted up. The clock counter 32 thus cycles interrogating the buttons B1–B8 to determine if a switch has been actuated by the examiner.

When one of the buttons is pushed, the clock counter 32 sequences, and if for example, button B3 has been depressed when the decoder output from decoder 38 goes to its low level then a low level signal occurs on line 25. This signal on line 25 couples to both the delay 44 and to the "read enable" input of the memory 36. The low level signal to the delay 44 causes the output from the delay to be at its low level for a period of approximately 1 second to compensate for any switch bounce that may occur upon button actuation. This low level signal couples to both gates 33 and 35 inhibiting any further counting of the clock counter 32 for this one second interval. Thus, the counter remains in an address position corresponding to the depressed button. This address is stored in section A of the memory 36 by the read enable signal from the common button line 25. The output from the delay 44 also couples to the gate 51 causing a clocking of the operations counter 30 to its next count position which is the "one" position shown in the truth table depicted hereinbefore. After the one second delay, when the output from the delay again reverts to its high level, the flip-flop 46 has its state changed by way of the NAND gate 60. The change of state of the flip-flop 46 now conditions the memory 36 to receive the next button address in section B of the memory.

The buttons B1–B8 are momentary buttons and thus once one of the buttons has been depressed and its address stored, the clock counter, after the one second delay of delay 44, continues to count cyclically until it detects a further button actuation. When the second button is actuated, a signal on line 25 activates the delay 44 and couples to the "read enable" of memory 36 causing the address of the second button to be stored in section B of memory 36. As with the actuation of the first button, when the second button is actuated, the counter 30 moves to its count "2" and the flip-flop 46 switches again by way of gate 60 so that the memory is now conditioned in section A for readout purposes. However, the display is still inhibited in this position of the operations counter.

After the second button has been depressed, the gate 63 which is a NOR gate passes a low enabling signal on line 64 to the input G1 of the decoder 40 thereby enabling the decoder for operation. The block counter 32 continues to count after the second button address is stored. When the decoder 40 decodes the count "8" a "low" level signal is coupled to the gate 51 to advance the operations counter to count "3", to switch the flip-flop 46 to read the first button address from the memory 36, and to the NOR gate 66. In state "3" of the operations counter the flip-flop 48 is not yet changed to its "down" state as the output C from the counter 30 is still at its low level causing the output of gate 68 to be high and the output of gate 66 to be low. A high transition to gate 48 is necessary to change its state.

When the clock counter, after the count of 8, reaches the zero count, gate 51 is again enabled to count the operations counter to its count "4". At this time the output C from the counter 30 is high and thus the line 24 is in its low enabling state thereby enabling the display 10.

In FIG. 3 the conductive legs L1–L8 and conductive circles C1–C7 are not conductively connected to each other. Separate lines connect from the decoder 56 by way of a transistor 57 associated with each output. When the address is received, one of the output lines goes to its "high" state causing the transistor 57 to conduct, thus grounding the preselected leg, such as leg L1. At this time the clock counter is in its zero position and thus the signals on lines 27 to the decoder 54 select the zero output which is driven to ground upon selection, holding transistor 55 off and thus applying a positive voltage level to the outermost LED associated with the selected conductive leg. As the clock counter counts from zero to a count of 8 the light emitting diodes coupled to the selected conductive leg are lit in sequence along a straight line toward the center of the display star. The circles C1–C7 are in sequence released from ground potential to cause the sequential illumination of the diode. When the clock counter reaches the 8 count, the center diode 67 is illuminated from the 8 output of the decoder 40, and at the same time this output causes the operations counter 30 to move to its next count which is the position "5" of the operations counter. When this occurs the gate 66 is enabled and has its output at its "high" state causing the flip-flop 48 to change state thereby enabling the gate 35 and inhibiting the gate 33. This now controls the clock counter to count down. At the same time the output from the decoder 40 by way of gate 60 conditions the flip-flop 46 and the memory 36 to the second button address so that now a different one of the conductive legs is selected. Upon each clock pulse, the clock counter 32 counts down and thus the diodes are illuminated in a straight path from the center of the display star to the outermost diode along the leg. When the clock counter 32 again counts down to zero the output from the decoder 40 by way of gate 51 counts the operations counter 30 to its next position which is position "6" causing both the B and C outputs from the counter to be at their high level thus enabling gate 70 and by way of gate 71 resetting the operations counter 30 to its zero count in readiness for further selections by the examiner of other line patterns. The signal from gate 71 is also coupled to the device 59 causing a resetting of all of the devices so that the next cycle of operation can start.

As previously mentioned the display matrix comprises 8 lines or legs L1–L8 arranged in a star pattern and 7 circles C1–C7 which are concentric around the mid-point of the star. Each of the light emitting diodes is positioned at the intersection of the legs and the circles, and each diode is energized by having a positive charge on the circle and a ground condition on the leg. The pressing of a first button selects a first line which is grounded and controlled from the output of the memory 36 through the decoder 56. The circles are then charged in succession, first in towards the center and then out from the center under control of the clock counter 32 by way of the decoder 54. The center diode 67 is energized by the clock counter directly from the decoder 40 causing one side of the diode to be grounded with a positive charge always maintained on the other side of the diode. FIG. 3 shows diodes LED associated with legs L7 and L8. It is understood that there are other diodes associated with the other legs L1-L6. Further, a series resistor R is connected with each of the diodes as depicted in FIG. 3.

In the testing procedure it is important to establish a rapport with the subject being tested. The subject should be seated comfortably at the table and should be instructed to focus attention directly on the screen. A sheet of test paper 20 as shown in FIG. 1 is placed on the table directly in front of the subject and aligned with either a front edge of the table or an alignment mark on the table itself. The subject is then told that some lines will be drawn on the display 16. The subject is instructed to reproduce or draw these lines himself just as they appear to him on the screen. Depending upon the age of the child it may be necessary to have some practice runs at drawing different line patterns. Also, if the subject is having some difficulty, the speed control knob may be used to slow down the rate of line display.

The test is given in basically four different sections. The first two sections comprise a number of different single line patterns generated by the examiner. In the first section the examiner determines if the speed of the line generation needs to be slowed down from its normal 0.25 second rate according to any mistakes made by the subject in this section. In a third section of the test the subject is requested to reproduce one of a plurality of different line patterns that have been displayed. In a last portion of the test, 2, 3, or 4 line patterns are shown and the subject is requested to draw these line patterns in the proper sequence as displayed.

The examiner preferably scores the test at a later time after the test has been completed. For this purpose a test scoring sheet is provided and the subject is scored in seven different categories. These categories are basic pattern reproduction, spatial orientation, line quality, directionality, mental processing time, short-term visual memory, and visual sequencing memory.

Pattern reproduction is the ability to draw an accurate reproduction of the line pattern while spatial orientation determines whether the pattern has been illustrated in the proper orientation on the work sheet. Line quality is the ability of the subject to reproduce the line pattern with good fine muscle control. Directionality is the ability to reproduce the pattern in the same direction as displayed and also measures the ability to reproduce the pattern on the same axis as displayed without rotations. The mental processing time is the time from the termination of the display to when the subject starts drawing. The short term visual memory is the ability of the subject to correctly reproduce one of a number of line patterns shown in succession. Finally, visual sequencing memory is the ability of the subject to reproduce a sequence of patterns correctly.

Figure 4A:
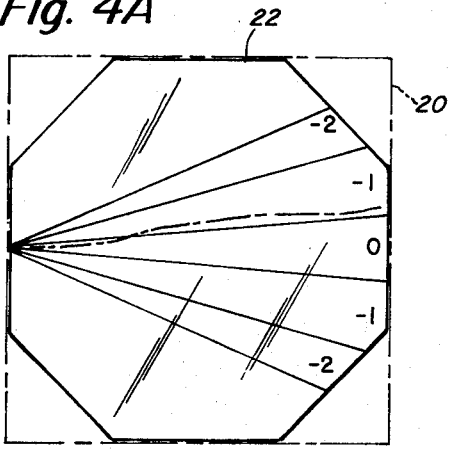
FIGS. 4A, 4B and 4C depict examples of overlay templates used by the examiner for scoring the parameters of pattern reproduction, spatial orientation, and line quality, respectively.
Figure 4B:
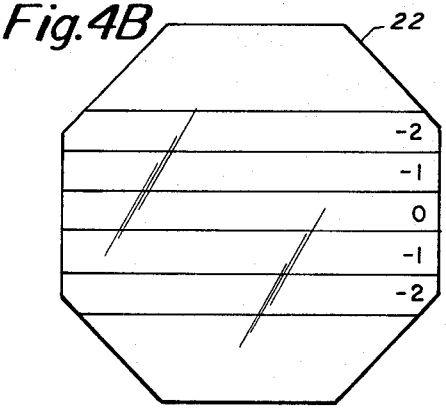
Figure 4C:
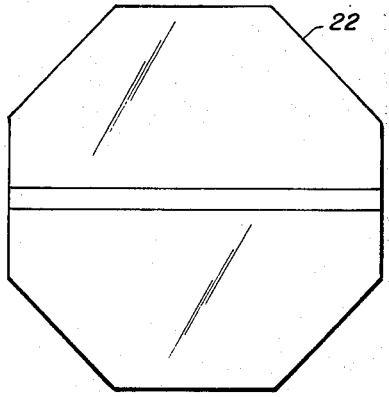

The scoring is facilitated with the use of templates 22 as depicted in FIGS. 4A, 4B and 4C. If the subject fails an item in the first two sections of the test a score of −4 is recorded in the basic pattern reproduction category. Also, if a pattern is unrecognizable and therefore unscorable using the following criteria, a −3 is scored for that item in each category in which it is unscorable.

For a straight line pattern, if the pattern is made up of more than one line with one or more sharp corners or more than one completely separated starting point, a score of −3 is registered. Otherwise, the template 22 shown in FIG. 4A may be used. This transparent template is placed on the test paper 20 so that the base of the angle on the template is at the beginning point of the line on the paper. The score can then be registered as shown on the template with scores of 0, −1, −2 or −3 depending upon the accuracy of reproduction of this pattern. It is noted that the transparent overlay or template has an octagonal shape so that the same template can be used for horizontal lines, vertical lines and also diagonal but straight lines.

For angular patterns of say 45°, 90° or 135°, if the pattern is made up of more than two lines, the item is scored −3. Otherwise the template is used corresponding to the particular pattern's angle. These different templates are not shown in the drawings, but it is understood that they are similar to the templates shown in FIG. 4A but are of angular shape having different scoring boundaries associated therewith as with the template of FIG. 4A.

The template shown in FIG. 4B is used for scoring spatial orientation. The template shown in FIG. 4B is placed directly in line with the work paper and the subject is graded accordingly. For example, if the subject produces a horizontal line at the very top of the paper rather than in the middle, a score of −3 is recorded rather than the desired score of 0.

FIG. 4C shows one template for scoring line quality. A score of −1 is registered if the line varies in straightness over its length disregarding short variations at the beginning or end of the pattern. The template of FIG. 4C shows the permissible variation. A score of −1 is also recorded if the line varies appreciably in intensity over its length disregarding short variations at its beginning or end. Also, a score of −1 is recorded if there is any break in the line including a break between the two parts of an angular pattern, or if there is more than one beginning point for a pattern.

The parameter of directionality is scored during the test with a score of −1 for each mistake in direction including starting the two parts of a pattern from the outside of the paper or rotating the entire pattern, say 90° or 180°, when drawn on the paper.

The mental processing time is a further parameter that is preferably recorded. The mental processing time is the time from when the pattern is completed on the screen to when the subject touches the paper with the pencil to begin drawing the pattern. This reaction time is preferably recorded in tenths of a second and is recorded for each pattern or sequence of patterns.

The short term memory parameter is scored by scoring −1 for every pattern the subject fails to reproduce correctly on the third section of the test.

The visual sequencing memory parameter is scored by scoring −1 for each pattern that the subject fails to reproduce correctly on the fourth section of the test.

The final scoring can be tabulated in a number of different ways such as by simply adding the individual scores to arrive at a negative total score or by subtracting these scores from a fixed positive value.

None of the existing tests enables scoring in up to seven categories as with the test of the present invention. In addition to a total test score it is also possible to make evaluations in each category so as to determine specific prerequisite reading skill deficiencies that the subject may have. For example, in the various sub-tests it may be found that the subject reverses certain line segments indicating a form of dyslexia.

It is also possible to establish normal scores or a range of normal scores in each category. Thus, for each subject that is tested, it is possible to compare that subject's score with what is considered to be a normal score to determine any deficiency. In this connection test results in accordance with this invention have also been compared with a national reading test, and there has been shown an extremely high correlation between the results obtained on the reading achievement test, and the test of this invention.

The purpose of the test of this invention which we have entitled "the line pattern test" is to assess a person's prerequisite skills for reading. These skills may be assessed in children prior to normal reading instruction as well as in adults or older children who have had some reading instruction.

The information obtained from the test can be used in many different ways. With pre-school children who have not had normal reading instruction, the test can be used to predict the potential reading ability of the child if given normal reading instruction. Once predicted, those children who are predicted to have a problem can be helped by the test results being used as a basis for remediation in identifying those areas where help is necessary. The test is useful in children to enable placement of the children in school or other reading programs as in remedial programs or in the case of children who show normal ability and normal prerequisites, to place such children in normal reading programs. The test can also be used as a basis for improving reading skills by identifying particular areas that may be causing something of a problem even though the persons tested have good reading ability. Thus a person with good reading ability can have his reading achievement improved by instruction in a particular area identified by the test.

From the above, it should be understood that the test is useful for pre-school children, elementary school children, high school children as well as post-high school adults who have had varying degrees of reading instruction prior to being given the test.

Once the problem areas are identified by the test, normal remediation techniques known to those skilled in the art are used to improve the ability of the person. In those cases where several remediation techniques are known, a practitioner working with the subject may select one of the several known methods. Moreover, it is possible to improvise new methods in an attempt to improve any of the seven different areas tested.

The results of the test of this invention have been found to be highly accurate and meaningful. The results correlate well with accepted achievement tests for reading. The results have been found to accurately identify normal or deficient readers as identified as such by other accepted tests. Differentiation between normal and deficient readers has been found to be extremely good. Thus the test has been found to have high accuracy and validity.

The apparatus of this invention may also be contained in a kit for use by a qualified examiner, which kit may include the display, the control means for generating the line patterns on the display, the subject's work papers, the transparent scoring templates, an examiner's test record for use during the test, and a line pattern test scoring sheet usually filled out by the examiner after the test has been taken. The examiner's test record shows that the test is preferably segregated into four different sections with the first two sections each including six patterns. The third section includes eight series of patterns, and the fourth section includes six series of patterns. The examiner records, for each pattern, the basic correctness of the pattern reproduction, a score for directionality, and a score for mental processing time. The scoring sheet is broken down into the seven categories previously mentioned, and each pattern or group of patterns is scored in one of more categories. Only the patterns in sections three and four are scored for short term visual memory and visual sequencing memory, respectively.

Having described one embodiment of the present invention, it should now become apparent to those skilled in the art that numerous other embodiments exist, all of which are contemplated as falling within the scope of this invention. For example, the line patterns have been disclosed as being produced along the legs of a star. These patterns may also be produced and displayed along the legs of, for example, a square or rectangle or other geometric shape. Also, these line patterns need not be straight line patterns but could conceivably include curved lines. Described herein is a moving line pattern. This line pattern may be displayed by means of a series of light emitting means or could be generated in any other way such as with the use of a CRT control to provide the proper traces to generate these line patterns.

What is claimed is:

1. Apparatus for testing the prerequisite reading capabilities of a subject comprising;
   means defining a display,
   control means coupled to the display for selectively generating on the display a plurality of different moving line patterns, one pattern at a time, with each pattern comprising at least one line segment,
   said control means comprising a control member manually controlled by an operator disposed remote from the display but in a position to note the accuracy of the reproduction by the subject,
   like ones of said line patterns being consistently generated from one display time to the next,
   said line patterns adapted to be copied by the subject being tested to assess prerequisite reading capabilities,
   means used by the subject disposed separate from the display, in non-overlying relationship with the display, and upon which the subject, after observation of the moving line pattern, copies the line pattern,
   and means for correlating the skills of the subject to reproduce the line pattern with prerequisite capabilities for reading of the subject.

2. Apparatus as set forth in claim 1 wherein said display comprises a screen and a plurality of individual light emitting means arranged in an eight-pointed star behind the screen.

3. Apparatus as set forth in claim 2 wherein said light emitting means each comprise a light emitting diode.

4. Apparatus as set forth in claim 2 wherein said control means includes a switch array operated by the examiner including switches corresponding to the points of the star.

5. Apparatus as set forth in claim 4 including a first counter operating as a program counter for enabling the display, a second counter capable of counting up and down, and a memory for storing an indication of the switches actuated by the examiner.

6. Apparatus as set forth in claim 5 wherein said display includes concentric conductive circles and conductive radially-arranged legs electrically isolated from the circles.

7. Apparatus as set forth in claim 6 wherein the memory indications select the legs and the circles are selected in sequence from the second counter.

8. Apparatus as set forth in claim 1 wherein said line patterns each comprise two line segments and said control means comprises means for controlling the generation of a first line segment followed by generation of the second line segment.

9. Apparatus as set forth in claim 8 wherein the control means includes a reversible counter counting in one direction to generate the first segment and in the opposite direction for generating the second segment.

10. Apparatus as set forth in claim 1 wherein said display includes a plurality of spatially disposed light emitting means arranged to provide all line patterns, said control means including control switch means for selecting particular patterns, memory means for storing data associated with the selected pattern, clock counter means for establishing rate of line generation and program means controlling the memory and clock counter means to enable the display for generation of the selected line pattern.

11. Apparatus as set forth in claim 10 wherein each pattern comprises two line segments and said display has a plurality of paths of light emitting means each path having an outer end and inner end, said memory for storing data identifying any two line paths, said memory controlling the illumination of the line pattern by in sequence selecting each path, said clock counter means controlled by the program means to count in one direction to control light illumination of one path and to thereafter count in the opposite direction to control light illumination in the other selected path.

12. Apparatus as set forth in claim 11 including a clear means coupled to the clock counter means, program means and memory.

13. Apparatus as set forth in claim 11 including a pair of bistable means a first one of which controls memory addresses and a second one of which controls the direction of counting of the clock counter means.

14. Apparatus as set forth in claim 11 including decoder means coupled from the clock counter means forming part of the programming means.

15. Apparatus as set forth in claim 1 wherein each generated line pattern is scored on basic pattern reproduction, spatial orientation, line quality, directionality, mental processing time, short term visual memory, and visual sequencing memory.

16. Apparatus as set forth in claim 1 wherein said means for correlating includes means for determining the accuracy with which the directionality of the reproduced line pattern is copied.

17. Apparatus as set forth in claim 1 wherein said control means includes memory means for providing substantially exact repeatable generation of each line pattern.

18. Apparatus as set forth in claim 1 wherein said line patterns include horizontal, vertical and angular line segments at least one type of which is used in each and every line pattern.

19. A method of testing the prerequisite reading capabilities of a subject, comprising the steps of displaying, at one time, one of a number of different moving line patterns by electrical display, providing the capability of changing the speed of the moving line patterns, like ones of said line patterns being consistently generated from one display time to the next, positioning the subject to view the display to enable the subject to copy at a place remote from the dislay each displayed line pattern, scoring the subject on the accuracy of his copying the line patterns and comparing the score of the subject with a predetermined normal score to determine any prerequisite reading skills deficiency of the subject being tested.

20. A method as set forth in claim 15 wherein a set of moving line patterns are generated and the subject is required to copy less than all line patterns of the set.

21. A method as set forth in claim 15 wherein a set of moving line patterns are generated and the subject is required to copy all moving line patterns only after all have been displayed.

22. A method as set forth in claim 15 wherein a set of moving line patterns are generated and the subject is required to copy less than all patterns but only after all have been displayed.

23. A kit for us in testing the reading ability of a subject comprising;
   a display to be viewed by the subject,
   a control means coupled to the display for selectively generating on the display a plurality of different moving line patterns, one pattern at a time with each pattern comprising at least one line segment,
   variable speed clock means for varying line speed motion,
   at least one work sheet disposed remote from the display upon which the subject can, after observation of the moving line pattern, reproduce a line pattern,
   transparent overlay means for scoring the work sheet,
   and means upon which the scores may be recorded.

24. A method of testing the prerequisite reading cabability of a subject comprising the steps of;
   displaying, in sequence, a plurality of individual different moving line patterns by electrical display means, including displaying the same patterns consistently from one display time of said pattern to the next,
   providing the capability of changing the speed of the moving line pattern,
   positioning the subject to view the display so that the subject responds to each displayed moving line pattern by copying at a location remote from the display each line pattern, and correlating the subject's response with a predetermined normal response to evaluate prerequisite reading skills.

* * * * *